United States Patent [19]

Urbas et al.

[11] Patent Number: 5,252,962
[45] Date of Patent: Oct. 12, 1993

[54] SYSTEM MONITORING PROGRAMMABLE IMPLANTABLE TRANSPONDER

[75] Inventors: Donald J. Urbas, Evergreen; David Ellwood, Golden, both of Colo.

[73] Assignee: Bio Medic Data Systems, Maywood, N.J.

[21] Appl. No.: 562,300

[22] Filed: Aug. 3, 1990

[51] Int. Cl.⁵ .............................................. G08C 19/16
[52] U.S. Cl. ........................... 340/870.17; 340/825.54; 340/573; 128/903
[58] Field of Search ...................... 340/870.17, 825.54, 340/505, 573, 572, 825.31, 825.69; 342/44, 50, 51; 128/903; 119/51.02; 307/465; 455/19

[56] References Cited

U.S. PATENT DOCUMENTS

| | | | |
|---|---|---|---|
| 4,114,151 | 9/1978 | Denne et al. | 455/19 |
| 4,631,708 | 12/1986 | Wood et al. | 340/825.54 |
| 4,730,188 | 3/1988 | Milheiser | 340/825.69 |
| 4,737,967 | 4/1988 | Cahalan | 340/310 A |
| 4,857,893 | 8/1989 | Carroll | 340/825.54 |
| 4,865,044 | 9/1989 | Wallace et al. | 128/903 |
| 4,870,304 | 9/1989 | Bloker et al. | 307/465 |
| 4,992,794 | 2/1991 | Brouwers | 342/51 |
| 5,028,918 | 7/1991 | Giles et al. | 340/825.54 |
| 5,105,190 | 4/1992 | Kip et al. | 340/825.54 |

FOREIGN PATENT DOCUMENTS

| | | |
|---|---|---|
| 0101125 | 2/1984 | European Pat. Off. . |
| 8704900 | 8/1987 | European Pat. Off. . |
| 0261081 | 3/1988 | European Pat. Off. . |
| 2070393 | 9/1981 | United Kingdom . |
| 2077556 | 12/1981 | United Kingdom . |
| 2163324 | 2/1986 | United Kingdom . |
| 2164825 | 3/1986 | United Kingdom . |

*Primary Examiner*—Donald J. Yusko
*Assistant Examiner*—Michael Horabik
*Attorney, Agent, or Firm*—Blum Kaplan

[57] ABSTRACT

A passive transponder includes a receive antenna for receiving an input signal. A frequency generator and modulator receives the input signal and outputs a data carrier signal having a frequency independent of the input signal frequency. A programmable memory and thermistor are provided to produce user ID data and temperature data which is combined with the output signal.

23 Claims, 7 Drawing Sheets

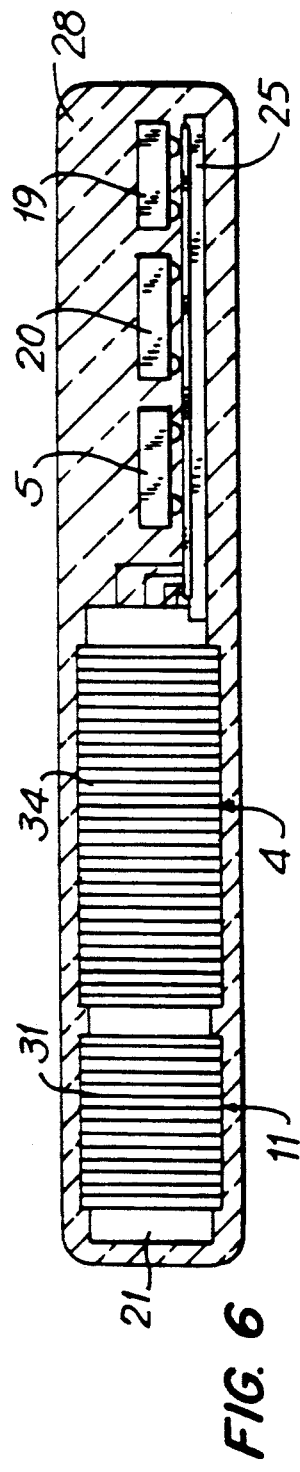
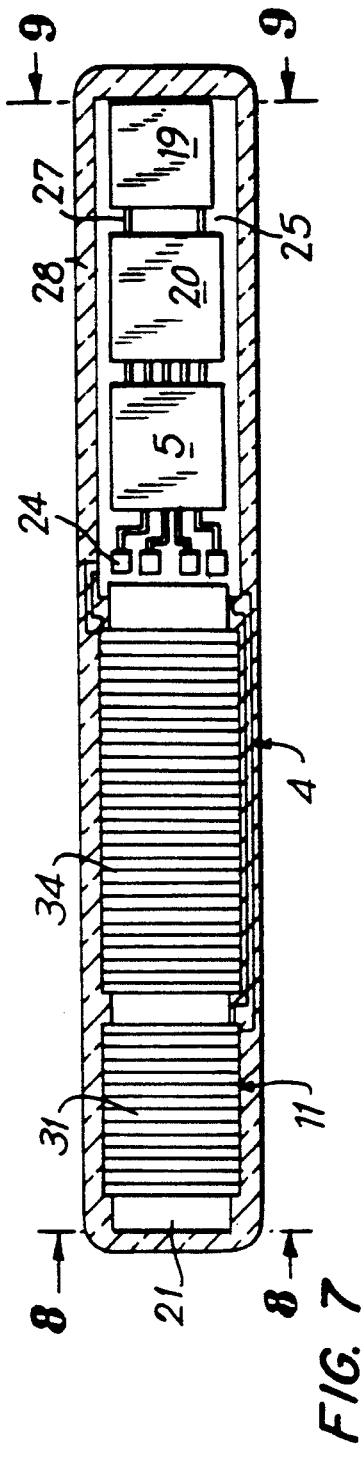
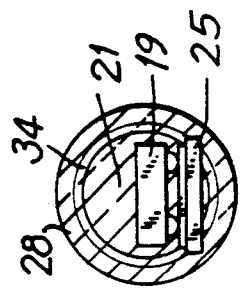
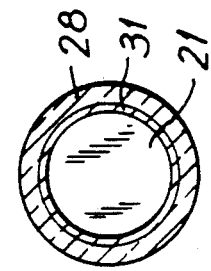

SYSTEM MONITORING PROGRAMMABLE IMPLANTABLE TRANSPONDER

BACKGROUND OF THE INVENTION

This invention is directed to a passive transponder and, in particular, to a passive transponder which is programmable after completion of manufacture utilized for monitoring the characteristic of the host into which it is embedded, and more in particular for identifying an animal and its characteristics.

Transponders and scanner systems are well known in the art. These systems include an interrogator which transmits and receives signals from a passive transponder. One such use is a transponder embedded in an animal. The prior art system known from U.S. Pat. No. 4,730,188 includes an antenna which transmits a 400 KHz signal which is received by the transponder embedded in the animal and returns a divided signal of 40 KHz and 50 KHz. This signal is coded in accordance with a combination of 40 KHz and 50 KHz portions of the transmitted signal to correspond to a preprogrammed ID number stored in a chip contained within the passive transponder. The ID number is preprogrammed at the time of manufacture. This ID number allows identification of the animal in which the transponder is embedded. The scanner then inputs this coded ID number into a microcomputer for processing.

The prior art transponders have been less than completely satisfactory because the amount of information which may be transmitted thereby was limited to the preprogrammed identification numbers contained therein. Accordingly, in a contemplated use such as animal identification, the user must use the preprogrammed identification number to identify the test animal. However, identification numbers are usually used as shorthand manner for presenting data concerning the animals. This requires that the user match his animal information to the preassigned transponder identification number resulting in an increase of time and effort. Additionally, this prior art device is unable to automatically transmit system status information, such as muscular pressure or temperature of the animal. Accordingly, the amount of information transmitted is quite small.

Because the transponders divide the received signal, a high frequency received signal must be broadcast to the transponder so that the divided signal will have a high enough frequency to transmit information. These higher frequencies are regulated by the FCC, therefore, the amount of power which can be supplied to the transponder, and in turn the read distance is limited. Additionally, because the transponder transmit antenna operates at 40 KHz, it is subject to background noise interference from television monitoring screens or computer CRTs which by necessity are normally present since they are used in conjunction with microprocessors which are used during scanning. These monitors also operate utilizing a 40 KHz and 50 KHz RF signal. Because these monitors have a high power output relative to the antenna they interfere with the operation of the interrogator when the interrogator is used in proximity to computers and other various monitors.

Therefore, a passive transponder which simultaneously senses an environmental condition and transmits this information along with user programmable identification information in a manner which is less susceptible to background noise interference is provided by the instant invention.

SUMMARY OF THE INVENTION

Generally speaking, in accordance with the instant invention, a passive transponder which identifies, simultaneously senses and transmits a condition to be sensed, such as the internal temperature or the like of an object is provided. The transponder includes a receive antenna for receiving the interrogator signal. The transponder is driven by the interrogator signal. A sensor circuit disposed within the transponder measures the condition to be sensed of an animal in which the transponder is embedded. A data sequencer receives the interrogation signal and enables the sensor circuit to output a signal representative of the condition to be sensed. The data sequencer causes the signal representive of the condition to be output over a transmit antenna contained within the transponder.

In one embodiment of the invention, the transponder also includes a programmable memory circuit which may be programmed with a user selected identification code through use of a signal received by the transponder. The data sequencer enables both the sensor circuit to output the temperature and the programmable memory to output an identification code in sequence. A frequency generator and modulator is provided for receiving the signal representative of the condition to be sensed and the identification code and modulating the data to be output on an output carrier signal in response to the input signal. The output signal frequency is independent of the input signal frequency which may be less than 10 KHz.

Accordingly, it is an object of the instant invention to provide an improved passive transponder.

A further object of the invention is to provide a passive transponder which simultaneously senses and transmits the internal temperature of an object or animal into which it has been injected.

Another object of the invention is to provide a programmable passive transponder.

A further object of the invention is to provide a transponder which outputs a signal having a frequency independent of the frequency of the received signal.

Still another object of the invention is to provide a passive transponder in which the signal output by the transponder has a frequency greater than the frequency of the received signal.

Yet another object of the instant invention is to provide a passive transponder which is energized in response to interrogation signals having a frequency of less than 10 KHz.

Still other objects and advantages of the invention will in part be obvious and will in part be apparent from the specification and drawings.

The invention accordingly comprises the features of construction, a combination of elements and arrangement of parts which will be exemplified in the constructions hereinafter set forth and the scope of the invention will be indicated in the claims.

BRIEF DESCRIPTION OF THE DRAWINGS

For a fuller understanding of the invention, reference is made to the following description taken in connection with the accompanying drawings, in which:

FIG. 6 ,is a side elevation view of a transponder constructed in accordance with the invention;

FIG. 7 is a top plan view of a transponder constructed in accordance with the invention;

FIG. 8 is a sectional view taken along line 8—8 of FIG. 7; and

FIG. 9 is a sectional view taken along line 9—9 of FIG. 7.

DETAILED DESCRIPTION OF THE PREFERRED EMBODIMENTS

Figure 1:
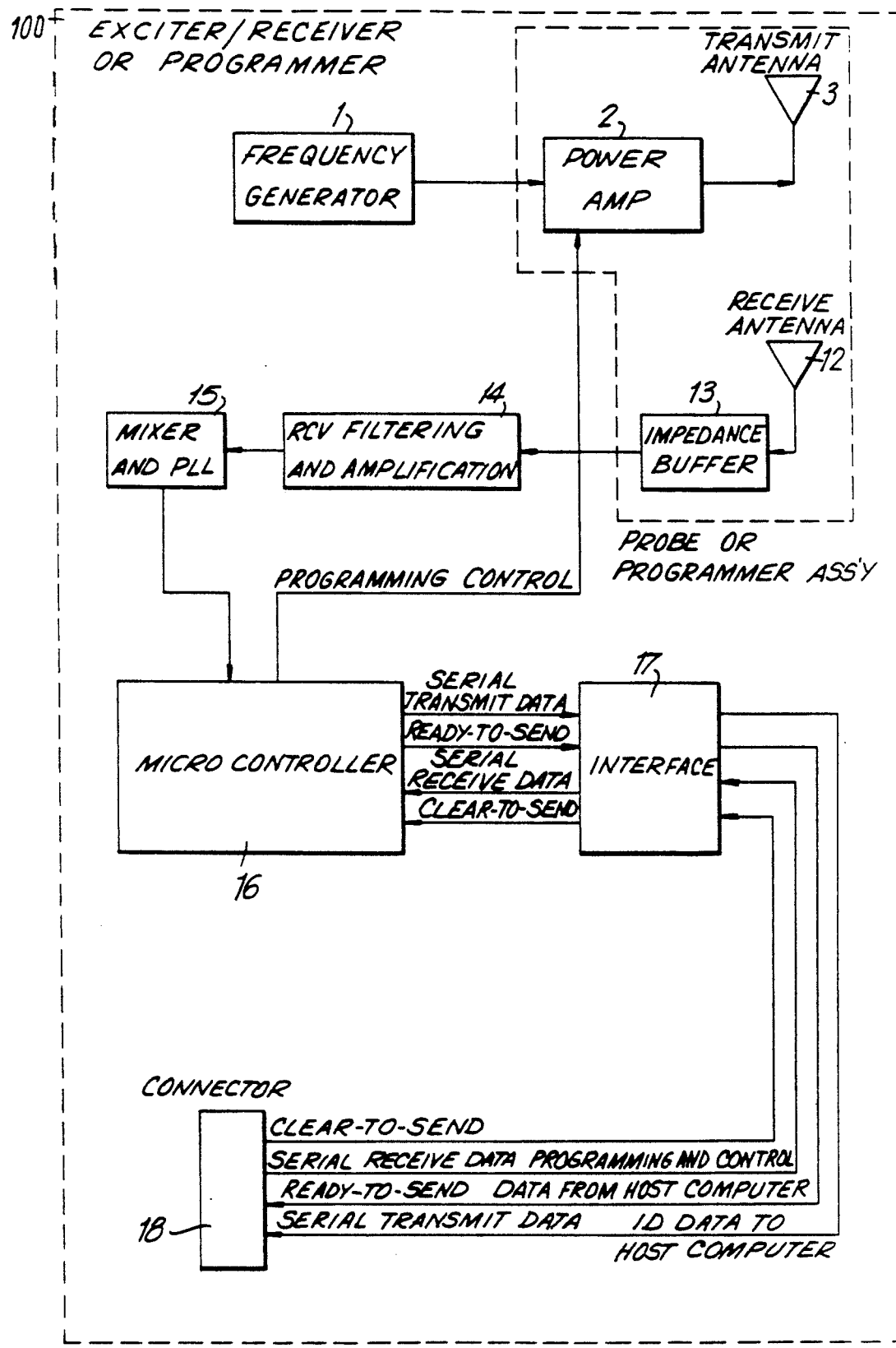
FIG. 1 is a block diagram of an interrogator constructed in accordance with the invention.
Figure 2:
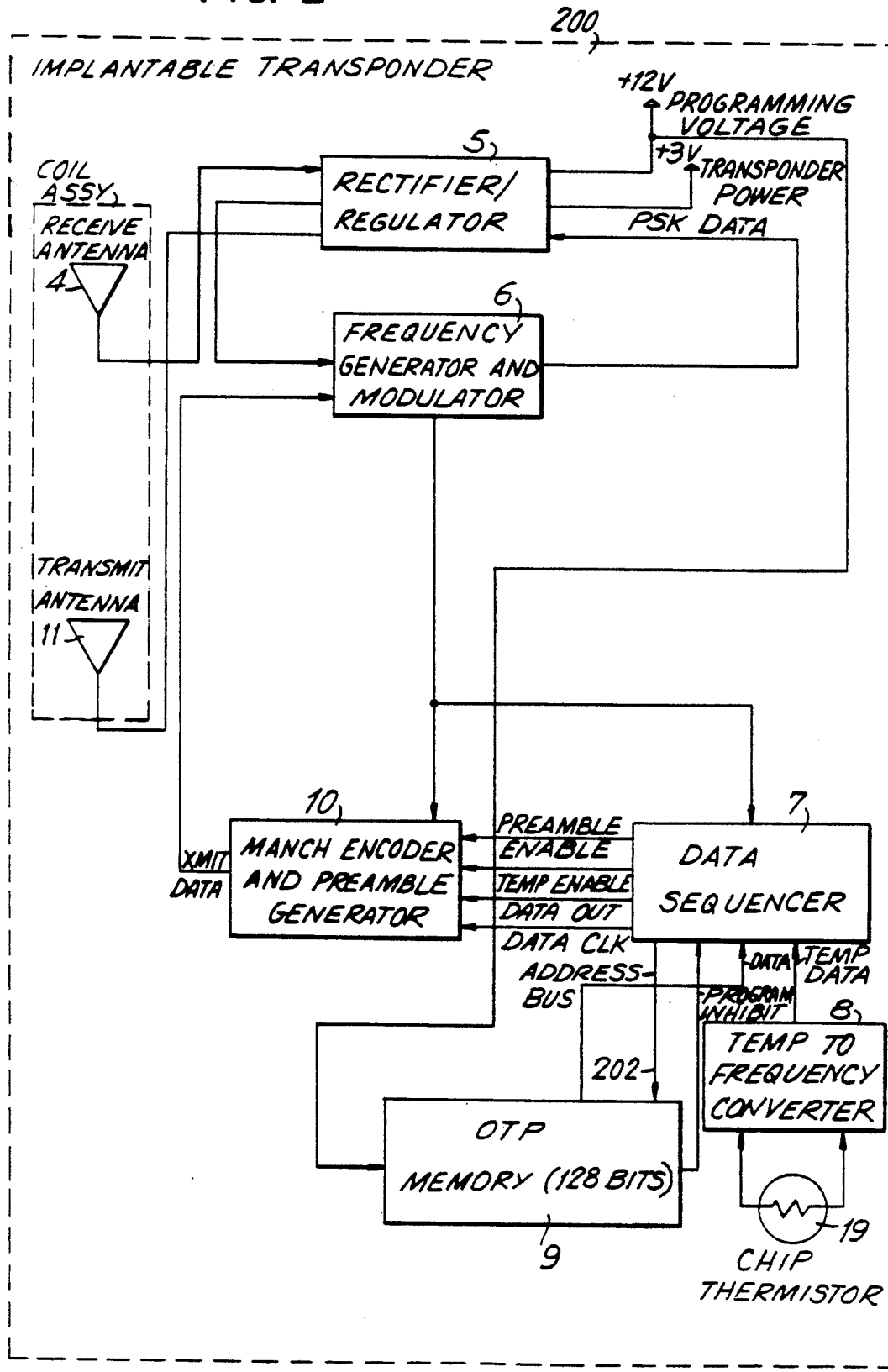
FIG. 2 is a block diagram of a passive transponder constructed in accordance with the invention.

Reference is first made to FIGS. 1 and 2 in which block diagrams of an exciter/receiver ("interrogator") 100 and implantable passive transponder ("transponder") 200 are provided. Interrogator 100 transmits an exciter signal to transponder 200. The exciter signal is received by transponder 200 and powers transponder 200. Once energized, transponder 200 is caused to output a data signal. This data signal includes a preamble portion, temperature data and identification code. The data signal is a PSK (phase shift keyed) signal with a 455 KHz carrier frequency. The transmission is a continuous, cyclic data stream containing the transponder ID and temperature information. This information is received by interrogator 100 and is demodulated, translated and input to a host computer for processing.

As will be described in greater detail below, transponder 200 includes a one time programmable memory 9. Programmer 100 which is coupled to a host computer receives an identification code that is to be programmed into transponder 200. Interrogator 100 modulates the amplitude of the excitation signal to communicate with transponder 200. When transponder 200 is in a program mode one time programmable memory 9 may be programmed by interrogator 100.

In an exemplary embodiment, interrogator 100 communicates with transponder 200 through inductive coupling known in the art from U.S. Pat. No. 4,730,188, which patent is incorporated herein by reference as if fully set forth herein. The interrogation signal is less than 10 KHz and more precisely 7109 Hz. The return data stream output by the transponder is output on a higher frequency carrier signal of 455 KHz.

A more detailed description of the invention is now provided. Description is made of the system in which transponder 200 already has been programmed and a user selected identification code has been stored in one time programmable memory 9. Interrogator 100 includes a frequency generator 1 which outputs a 7109 Hz signal. A power amp 2 receives the output signal and causes the signal to flow through the primary coil of a transmit antenna 3 which generates an excitation field at a frequency of 7109 Hz from exciter 100.

Reference is now made specifically to FIG. 2 in connection with describing the internal configuration of transponder 200. A receive antenna 4 mounted within transponder 200 receives the exciter signal from interrogator 100 and inputs a 7109 Hz signal to a rectifier/regulator 5. Rectifier/regulator 5 receives the AC signal from the receive antenna and rectifies the signal. The unregulated voltage is then regulated to 3 volts to power the digital circuitry contained within transponder 200. In an exemplary embodiment, rectifier/regulator 5 utilizes Schottky diodes to reduce the voltage drop. Rectifier/regulator 5 limits the voltage to protect the digital electronics. The rectified signal is then passed through a frequency generator modulator 6 and input to a data sequencer 7 and manchester encoder and preamble generator 10.

Data sequencer 7 receives as inputs the 7109 Hz signals, temperature data from a temperature to frequency converter 8 and the programmed ID data from one time programmable memory 9 and controls the sequencing of the cyclical transmitted data stream which includes the preamble, ID data and temperature data. A one time programmable memory 9 stores the ID data therein. When data sequencer 7 receives the 7109 Hz input signal, it first outputs a preamble enable signal causing manchester encoder and preamble generator 10 to output a data preamble. It then outputs the ID data stored in one time programmable memory 9. Data sequencer 7 sequentially accesses the address to be read from memory 9 through address bus 202 this causes memory 9 to output the data to data sequencer 7 which gates the data and outputs the ID data at the appropriate time to manchester encoder and preamble generator 10.

Figure 4:
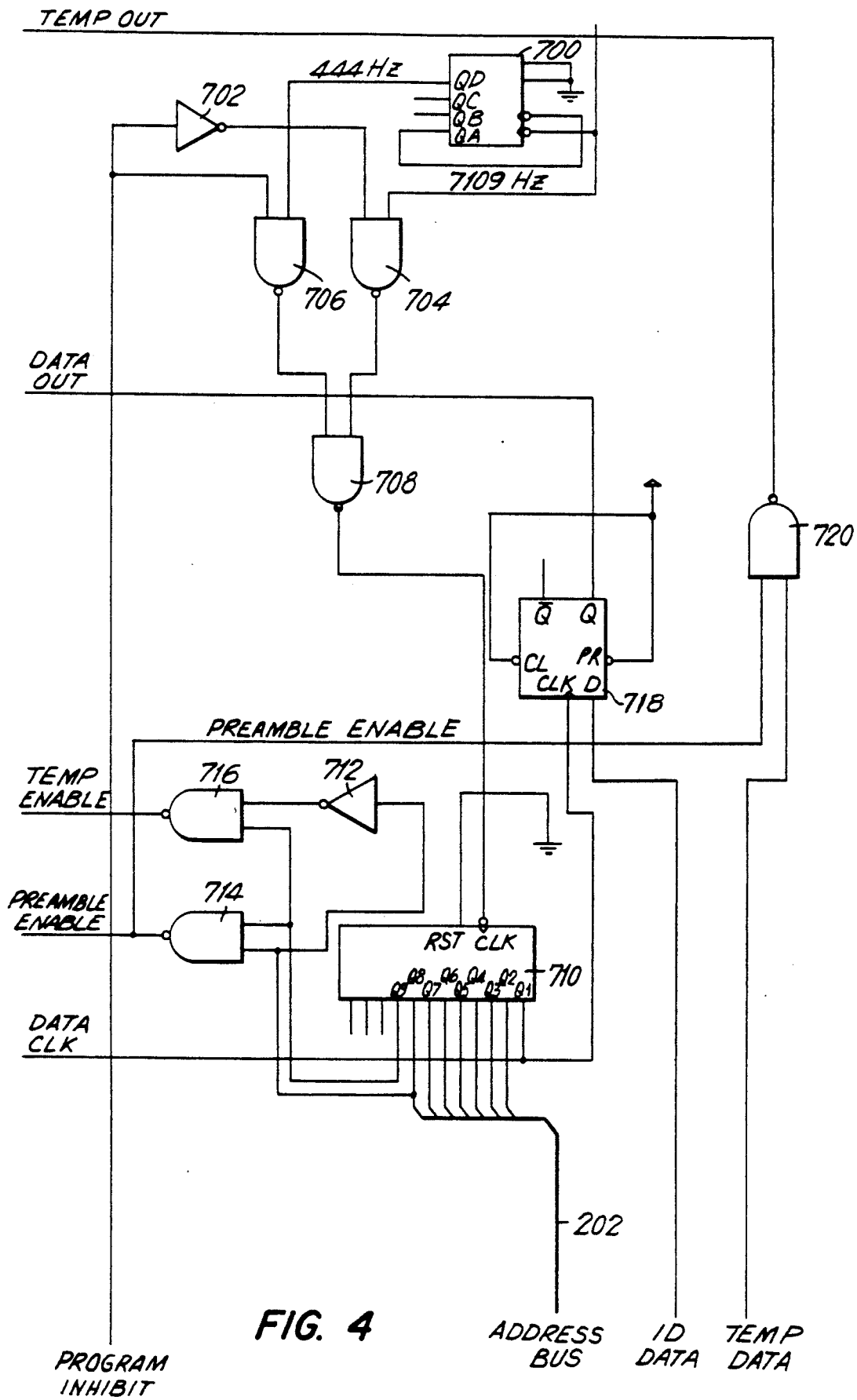
FIG. 4 is a circuit diagram for a data sequencer constructed in accordance with the invention.

Reference is now made to FIG. 4 in which a circuit diagram of data sequencer 7 is presented. Data sequencer 7 includes a counter 700 which receives the 7109 Hz signal, divides by 16 and outputs a 444 Hz signal. One time programmable memory 9 outputs a program inhibit signal indicative of whether the memory has been programmed by the user with an ID data. The program inhibit signal has a value of 0 if the memory has already been programmed and a value of 1 if it has not been programmed. A first NAND gate 704 receives the 7109 Hz signal output by frequency generator and modulator 6 as a first input and the inverted program inhibit signal as a second input. A second NAND gate 706 receives the 444 Hz clock signal and the program inhibit signal as inputs. The outputs of both NAND gate 704, 706 are input to a third NAND gate 708 which gates each of the outputs and produces a clock signal having a value of either 444 Hz or 7109 Hz as an output.

A binary counter 710 receives the output of NAND gate 708 and utilizes this signal as the internal timing signal. Binary counter 710 provides a data clock at its output Q1 of 3555 Hz when a signal of 7109 Hz is received. Binary counter 710 also sequentially accesses the addresses within programmable memory 9 through the address bus at this clock rate.

During the reading of data from memory 9, the accessing of each memory causes ID data to be output by memory 9. This data is then input to a clock 718 which receives as a clock input the 3555 Hz data clock output by binary counter 710. This is to synchronize the data being output by memory 9 with the transmit sequence as represented by the data clock.

A NAND gate 714 and a NAND 716 are provided to gate the transmission of the preamble, ID data and temperature data portions of the cyclical transmitted data stream. NAND gate 714 receives the output of Q8 as one of its inputs and the output of Q9 as its other and outputs the preamble enable signal. NAND gate 716 receives the inverted output of Q8 and the output of Q9 and outputs the temperature enable signal so that the two NAND gates will not enable the transmission of the respective data simultaneously. Additionally, a NAND gate 720 utilizes the preamble enable signal to gate the temperature data being produced by temperature to frequency converter 8 so that when the preamble enable is low, the temperature waveform is blocked.

During the read operation, the program inhibit signal has a low value, therefore, its inverted signal is high. Because one input of NAND gate 706 is 0 (the program inhibit value), it will continuously produce a high output. Whereas the inputs of NAND gate 704 are a continuously high signal and the oscillating waveform signal of the received 7109 Hz signal, the output of NAND gate 708 will be a 7109 Hz clock signal. Binary counter 710 utilizes this signal producing a data clock of 3555 Hz and a read out rate of 3555 Hz.

In an exemplary embodiment, if the output of Q9 is low the preamble data is output and then the program ID data. Once the value of Q9 goes high, the preamble enable goes high allowing the temperature data to be transmitted through NAND gate 720. During the time Q9 goes high, the EPROM of memory 9 is still sequenced. However, the ID data is not output by the manchester encoder and preamble generator 10.

To obtain the temperature data portion of the output signal, a chip thermistor 19 is provided which outputs a resistance in response to changes in temperature. The resistance is input to temperature to frequency converter 8 which converts the resistance to a frequency which is input to data sequencer 7. In an exemplary embodiment, temperature to frequency converter 8 is an RC oscillator that is controlled by the resistance of thermistor 19. The frequency of the oscillator increases with temperature. The oscillator has an approximate frequency of 160 KHz at 36° C. Data sequencer 7 gates this frequency and outputs the signal to manchester encoder and preamble generator 10 at the appropriate time allowing manchester encoder and preamble generator 10 to output a cyclically transmitted data stream which includes the preamble, ID data and temperature/frequency data.

Manchester encoder and preamble generator 10 receives the 7109 Hz signal and responds to the preamble enable, temperature enable signals, data out and data clock signal produced by data sequencer 7. When the preamble enable signal produced by data sequencer 7 is high it encodes the data being transmitted by data sequencer 7. The 7109 Hz clock is selected as the manchester clock and the data out signal is always high producing an output twice the normal data clock frequency. This allows a simple means of detecting the beginning of the cyclical data sequence. In a first stage, the manchester clock is mixed with the ID data to produce manchester encoded preamble and ID data signal. In a next step, when the temperature enable signal is high, the manchester encoder and preamble generator 10 replaces the manchester encoded ID data with the temperature data completing one cycle of data transmission. This data is transmitted at 3555 baud to frequency generator and modulator 6. By way of example, the preamble, ID data and temperature data are produced in this order. However, as the entire output signal is continuous and cyclical, the temperature data may be output first.

Frequency generator and modulator 6 receives the data to be transmitted from manchester encoding and preamble generator 10 as well as the received clock signal of 7109 Hz. Frequency generator and modulator 6 multiplies the input clock signal by 64 to produce a transmit carrier frequency of 455 KHz to output a 455 KHz carrier signal containing the data. This carrier signal is phase shifted by 180° when the transmitted data changes state to output a phase shift keyed signal.

Figure 3A:
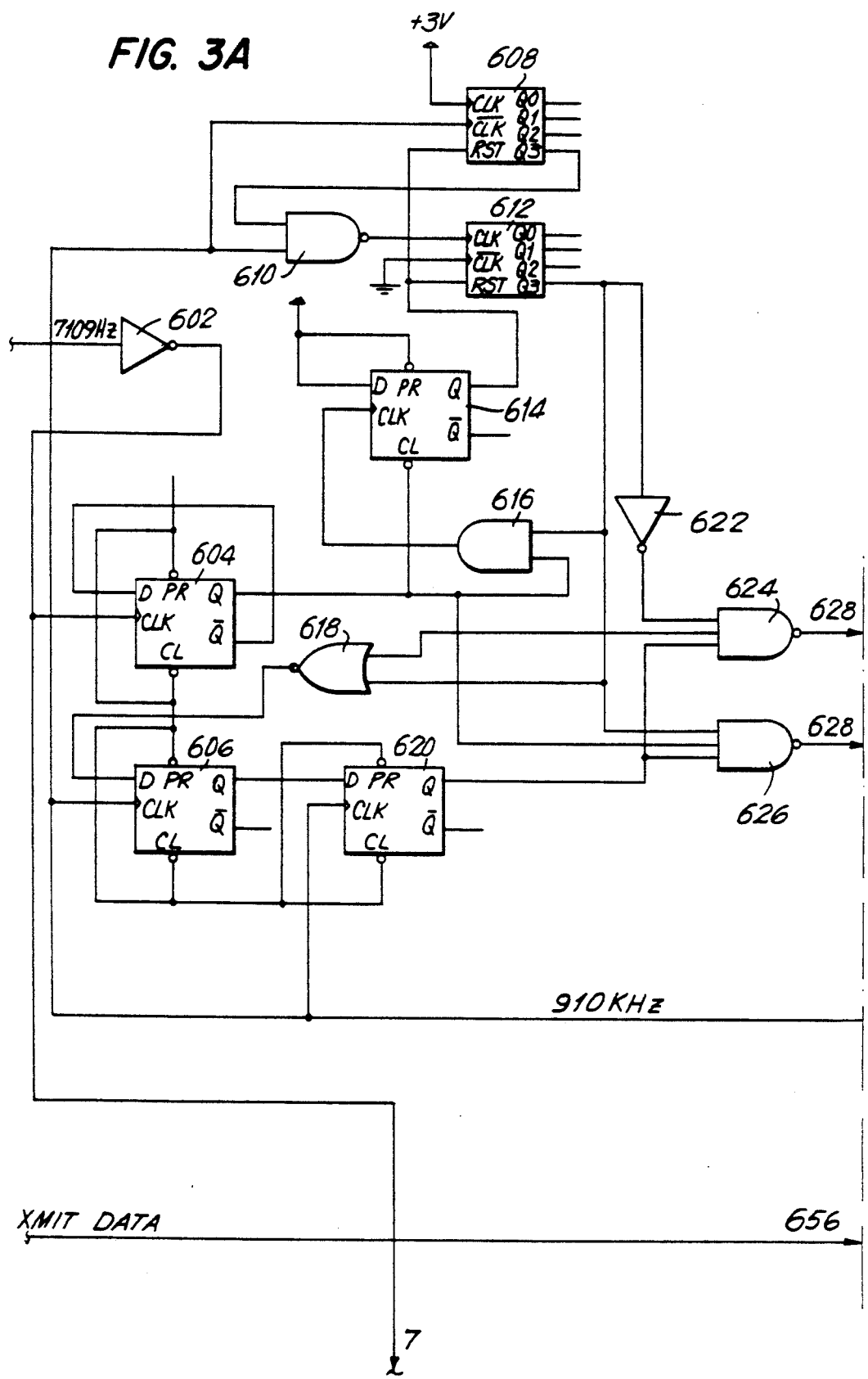
FIGS. 3a, 3b are respective halves of the frequency generator and modulator of FIG. 2 constructed in accordance with the invention.
Figure 3B:
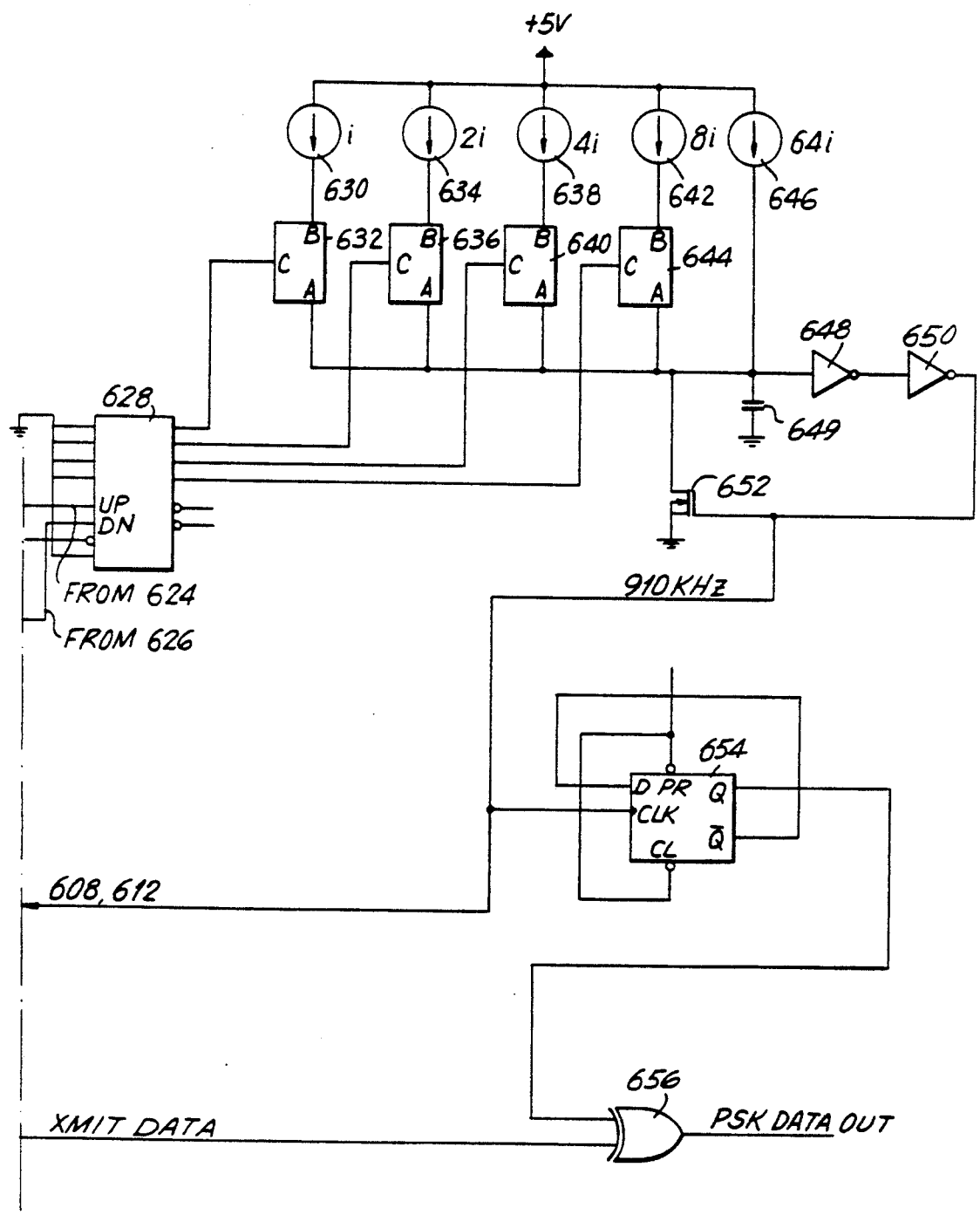

Reference is now made to FIG. 3a and 3b, wherein a circuit diagram of frequency generator and modulator 6 is provided. The circuit shown in FIG. 3a operates digitally on the received 7109 Hz signal and provides an input to an analog portion of the circuit shown in FIG. 3b. The frequency generator and modulator multiplies the frequency of the received clock (7109 Hz) to produce a 455 KHz carrier signal by comparing an internal digitally controlled oscillator with the period of one cycle of the received clock signal.

An analog oscillator is provided having a capacitor 649 which is charged by a combination of voltage sources 630, 634, 638, 642 and 646 having values of $i$, $2i$, $4i$, $8i$ and $64i$ respectively. The current is input to capacitor 649 to charge. Capacitor 649 is coupled to inverters 648, 650 arranged in series. The output of inverter 650 is input to a MOSFET transistor 652 for discharging capacitor 649. This continuous charge and discharge provides an oscillator of a certain frequency. The rate of oscillation is based on the current sources so that the amount of charge stored in capacitor 649 as a function of the amount of current and then discharged by transistor 652 causes oscillations within the circuit producing pulses at about 910 KHz. In an exemplary embodiment capacitor 649 has a value of 10 pF.

The 910 KHz signal is input to a divide by 256 circuit which includes NAND gate 610 and two binary counters 608, 612. The 910 KHz signal is input into binary counter 608 and is also one input of NAND gate 610. The second input of NAND gate 610 is the divided output Q3 of binary counter 608. The output of NAND gate 610 is input as the clock input of binary counter 612 so that the output Q3 is a signal having a frequency of about 3554.68 Hz.

At the same time, the received 7109 Hz signal is received by frequency generator and modulator 6 and is inverted by an inverter 602. The inverted received signal is input to a flip flop 604 as the clock input. Flip flop 604 is a divide by 2 so that its Q output is a signal having a frequency of about 3554.5 Hz. This signal is asynchronous with the 3554.68 signal of the divide by 256 circuit. A NOR gate 618 receives the two signals as does a NAND gate 616. A comparison is made between the two signals to determine which occurs first and adjustments are made.

To prevent toggling back and forth between one coming before the other at NAND gate 616, a delay circuit is provided. The delay circuit includes the flip flop 606 providing an input to the flip flop 620. Flip flop 606 receives the 910 KHz signal as the clock input and provides a Q output to flip flop 620 received at the D input of flip flop 620. Flip flop 620 again clocks this signal with the 910 KHz pulses of the oscillating clock formed about capacitor 649. This delays the output of flip flop 620 by at least one cycle of the 910 KHz pulse signal.

A pair of NAND gates 624, 626 are provided. The output Q of flip flop 604 representing the divided down received signal having the 3554.5 Hz frequency is input to both NAND gates 624, 626 as is the delay Q output of flip flop 620. However, NAND gate 624 receives the inverted output of the divide by 256 circuit (the 3554.68

Hz signal) while NAND 626 receives the actual signal itself. The outputs of NAND gate 624, 626 control are input to an updown counter 628. The outputs QA-QD of updown counter 628 control the amount of current flowing from each current source through switches 632, 636, 640, 644 respectively to the capacitors 649.

The relative outputs of NAND gates 624, 626 control whether the amount of current fed to capacitor 649 should be increased or decreased thus affecting the frequency of the pulses produced. This is a delayed function so that no matter which signal, the divided receive signal or the divided oscillator signal goes high first it will be delayed before the gates 624, 626 are able to determine whether the count of up down counter 628 should go up or down. If the output Q of flip flop 604 goes high first, it is delayed by flip flops 606, 620. If at the same time the output at Q3 of binary counter 612 is low, the input of NAND gate 624 would be high while the input of NAND gate 626 would be low. The output of NAND gate 624 would cause an up pulse at counter 628.

The counting of flip flops 608, 612 are controlled by flip flop 614 which receives the Q output of flip flop 604 as its clear. Flip flop 614 in turn controls the resetting of flip flops 608, 612 and thereby controls the output of the divide by 256 circuit. Additionally, the clock input of flip flop 614 is the output of AND gate 616. If the output Q3 is 1, the Q output of flip flop 614 goes high causing output Q3 of flip flop 612 to go low again re-starting the whole process. Counting can only occur when the Q output of flip flop 604 is low.

If it is determined by NAND gates 624, 626 that pulses are not being output at 910 KHz corrections are made by updown counter 628. Switches 632, 636, 640, 644 are analog switches which allow the current from the respective current source 630, 634, 638, 642 to be output to the capacitor 649 to charge it up at a faster rate thereby increasing the frequency of pulses. As the need for an increased frequency arises, the number of switches 632, 636 and the like which will be turned on to allow current to pass to capacitor 649 increases sequentially until the frequency of the pulses is sufficient.

A divide by 2 flip flop 654 receives the 910 KHz pulse as a clock signal and outputs as a Q output a 455 KHz signal. The 455 KHz signal is the carrier frequency for the data which is transmitted by transponder 200. An exclusive OR gate 656 receives the 455 KHz signal and the data to be transmitted including the preamble, ID data and temperature data as a second input. The exclusive OR gate shifts the phase of the carrier signal by 180° in response to the data so that a phase shift keyed data output signal is produced by exclusive OR gate 656. This phase shift keyed signal is then transmitted to interrogator 100 where it is operated upon.

By multiplying the received clock by 64, a transmit carrier frequency of 455 KHz is obtained. By digitally comparing the period of 64 cycles of the internal digitally controlled oscillator with the period of one cycle of the received clock, a very inaccurate frequency source can be synchronized with a very accurate frequency source to produce an accurate carrier frequency at a much higher frequency without imposing limits on the frequency values. As disclosed above, this is accomplished by determining whether the received clock cycle is shorter or longer than the 64 cycles of the oscillator. If the received clock cycle is shorter, then the oscillator frequency is too low and a up pulse will be generated output to an updown counter controlling the current sources to the capacitor. If the received clock cycle is longer, then the oscillator frequency is too high and a down pulse is generated and output to the updown counter.

The phase shift keyed data is output through rectifier/regulator and a transmit antenna 11. A 455 KHz field is produced which is received by receive antenna 12 of interrogator 100.

The received signal is input into an impedance buffer 13 which buffers the high impedance of the tuned receive coil forming receive antenna 12 so that the much lower impedance of the receive filter does not reduce the received signal strength. The impedance matched signal is an input to a receive filtering and amplification circuit 14. Receive filter amplification circuit 14 filters out unwanted signals and amplifies the received signal for further processing.

In an exemplary embodiment, receive filtering and amplification circuit 14 uses a multiple pole ceramic band pass filter with a +/−15 KHz pass bandwidth and 60 dB attenuation in the stop band to filter out unwanted signals. The signal is then amplified with a gain of 40 dB. The circuit is shielded and the power supply are isolated to keep external electromagnetic influences from corrupting the received signal.

The amplified received signals are then input to a mixer and phase locked loop 15. The mixer receives the received signal with a 410 KHz signal to produce a base band received signal at 45 KHz. The phase locked loop produces a positive pulse with every 180° phase shift of the received signal. These pulses are then input to a micro-controller 16 where the received ID data is reconstructed and the temperature dependent frequency forming part of the output data stream from transponder 200 is detected and analyzed.

Micro-controller 16 reconstructs the ID data portion of the received signal and temperature information from the frequency pulses output by temperature to frequency converter 8. Microcontroller 16 outputs data and appropriate protocol signals which may include a ready to send signal indicating that the data is about to be sent, the transmitted data is then sent in serial fashion to an RS 232 interface 17 which converts the data from digital levels to RS 232 levels. This converted information is then passed through a connector 18 to the host computer at which the data is to be processed.

By providing a passive transponder which contains a chip thermistor and, a temperature frequency converter, it becomes possible to monitor the temperature of the animal in which the transponder has been implanted. Temperature is utilized merely by way of example. Through use of a data sequencer as described above, other system status characteristics, such as muscular pressure, light levels or other fluid conditions may be continuously monitored and transmitted to a remote host computer. Additionally, by providing a frequency multiplier within the transponder it becomes possible to use an interrogation signal of less than 10 KHz, a non-FCC regulated frequency, making it possible to increase the power utilized to send this signal thus allowing increased read distances between the inductively coupled interrogator and transponder. Further, by utilizing a frequency generator and modulator in which an internal digitally controlled time period is compared with one cycle of the received clock and operated thereon, a very inaccurate frequency source, the internally generated oscillator clock, can be synchronized with a very accurate frequency source, the received signal, to produce an accurate frequency source at a much higher frequency which is more suitable for transmitting the more complex transmit data stream of the transponder.

PROGRAMMING

Figure 5:
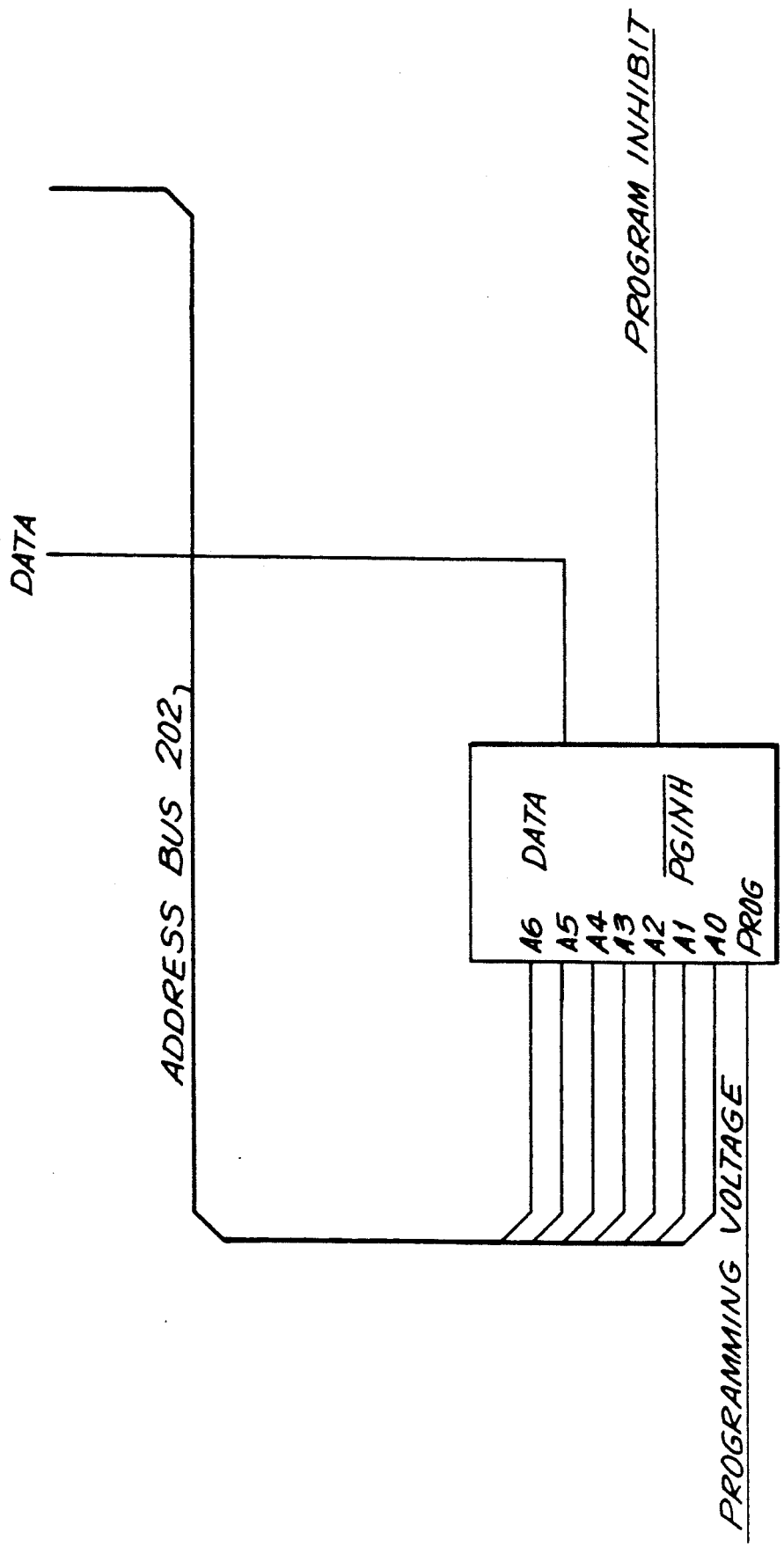
FIG. 5 is circuit diagram of the one time programmable memory constructed in accordance with the invention.

Reference is now made specifically to FIGS. 4 and 5 in which programming of transponder 200 is described. One time programmable memory 9 is an EPROM which always has its output enabled. Before it has been programmed, it is in a program mode (program inhibit is high) as seen from FIG. 4. This causes data sequencer 7 to operate at an internal clock of 444 Hz. Prior to programming, each address of one time programmable memory 9 has a value of 1. The program inhibit signal causes data sequencer 7 to operate at an internal clock of 444 Hz. This clock causes counter 710 to operate at a slower 444 Hz speed causing the transmission of data to occur at the slower speed. Accordingly, when the carrier signal is produced at frequency modulator 6, the PSK data rate is lower than that discussed above when the already programmed ID code is utilized. This is due to the slower data clock of data sequencer 7. This lower rate is at 222 baud as opposed to 3555 baud utilized during normal data transmission.

Generally during programming interrogator 100 receives this different data rate and recognizes that programmable memory 9 has not been programmed. It then scans the ID portion of the data signal and compares its address for address with the ID number to be programmed into transponder 200. If the values for the address do not coincide, then the values are changed until the ID data that is stored in programmable memory 9 corresponds to that in the host computer.

More specifically, interrogator 100 in a manner almost identical to that discussed above with the exception of the slower data rate causes binary counter 710 to increment the address of the programmable memory which is presently being accessed. Initially all 128 bits in the EPROM are set at 1. If the value of 1 is not correct for the presently accessed address, the host computer causes micro-controller 16 to output a programming control signal to power amp 2. This causes power amp 2 to output a high voltage signal through transmit antenna 3 to receive antenna 4 of transponder 200. This high voltage signal becomes a 12 volt signal after processing by rectifier/regulator 5. This programming voltage is input directly through the PROG input of one time programmable memory 9 to change the value at the present address of the EPROM from a 1 to a 0. This process is repeated for each address of the EPROM. If the value of that address is correct as 1, it is merely scanned, not operated upon and then the binary counter advances to the next address. As each address is read, the value of that address is output through the DATA output of one time programmable memory 9 and is processed by data sequencer 7 as discussed above.

During programming mode, the program inhibit signal is 1. Accordingly, the inputs of NAND gate 706 and NAND gate 704 become switched from the above discussed reading mode. The input of NAND gate 706 is 1 and the 444 Hz signal so that the output of NAND gate 706 is a waveform having a frequency of 444 Hz. Additionally, the inputs of NAND gate 704 are now 0 and a waveform so that the output of NAND gate 704 will always be 1. Accordingly, the clock used by binary counter 710 during the programming mode is 444 Hz which results in a data clock of 222 Hz. The operation of the enable gates and the temperature gates are identical as that described above.

When the last address of the one time programmable memory 9 is programmed, the value is changed from 1 to 0. This causes the program inhibit signal which is output to change the internal clock of data sequencer 7 from the 444 Hz rate to the 7109 Hz rate. Accordingly, during the next interrogation by interrogator 100, interrogator 100 determines that it should not program transponder 200 based upon this new received PSK data rate.

To produce the programming control signal, power amp 2 is provided with a P channel power MOSFET causing 24 volts to be applied to the exciter primary. This causes a much more powerful excitation field to be generated. It is this high excitation field which causes the bit presently being accessed within transponder 200 to be programmed to 0. On the receiving end, rectifier/regulator 5 is provided with a Zener diode to limit the programming voltage to the 12 volts discussed above.

By providing a programmable memory which outputs an inhibit signal once each of its addresses has been programmed and a data sequencer having an internal data clock which functions at a different rate during programming and during reading, a one time programmable memory is provided which allows a programmer using the interrogator transponder system of the present invention to select his own non-erasable identification codes for the animal being monitored after manufacture of the transponder. Additionally, by utilizing a slower frequency signal during programming then during receiving, the efficiency of both programming and transmitting of information is enhanced.

Reference is now made to FIGS. 6-9 in which a transponder 200 constructed in accordance with one embodiment of the invention is provided. Transponder 200 includes a substrate 25. Rectifier/regulator 5 is mounted on substrate 25 along with a chip thermistor 19. A chip 20 housing the structures of frequency generator and modulator 6, data sequencer 7, temperature to frequency converter 8, one time programmable memory 9 and manchester encoder and preamble generator 10 is also supported upon substrate 25. Rectifier/regulator 5, chip 20 and chip thermistor 19 are electrically coupled to each other by connecting traces 27 deposited on substrate 25.

Receive and transmit antennas 4, 11 are formed about a ferrite rod 21. Transmit antenna 11 is formed by wrapping a coil 31 about ferrite rod 21. Receive antenna 4 is formed by a coil 34 wound about ferrite rod 21. Coils 31, 34 are coupled to rectifier/regulator 5 through bonding pad 24.

In an exemplary embodiment, transponder 200 is encapsulated in a glass capsule 28. The capsule is 0.500 inches to 0.750 inches long and has a diameter of 0.080 inches to 0.100 inches. The glass capsule may either be coated with a protective epoxy, replaced entirely with a protective epoxy or treated to prevent migration in animals.

Interrogator 100 may be housed in two distinct portions for ease of use. Power amp 2, impedance buffer 13, transmit antenna 3 and receive antenna 12 may be housed in a probe assembly as known from U.S. Pat. No. 4,526,177. The remaining structure of exciter 100 may be housed in a separate housing. Such differentiation of structure reduces any interference from microcontroller 16, frequency generator 1 or the host computer to either the transmit antenna 3 or receive antenna 12.

By forming the frequency generator and modulator, data sequencer, memory, temperature to frequency converter, and manchester encoder and preamble generator on a single chip, efficiencies in size and cost may be obtained. By forming the entire transponder less than 0.750 inches long and with a diameter of 0.10 inches or less, the entire assembly becomes implantable.

It will thus be seen that the objects set forth above, and those made apparent from the preceding description are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A passive transponder comprising encapsulation means including therein receive antenna means for receiving an input signal, transmit antenna means for transmitting an output signal to said signal source, programmable memory means for storing data received by said transponder from said signal source, said programmable memory means being programmed in response to said input signal after completion of manufacture of said transponder, said output signal including said data stored by said programmable memory means, and said output signal being generated in response to said input signal, said transponder transmitting the output signal at either one of a first baud rate allowing programming of said programmable memory means or a second baud rate preventing further programming of the programmable memory means dependent upon the status of said programmable memory means.

2. The passive transponder of claim 1, wherein said first baud rate is slower than said second baud rate.

3. The passive transponder of claim 1, wherein said programmable memory has a plurality of memory addresses and said programmable memory means outputs an inhibit signal once each of said addresses has been accessed during programming.

4. The passive transponder of claim 3, comprising data sequencing means; said data sequencing means receiving said input signal and said inhibit signal and generating a divided input signal having a frequency substantially less than said frequency of said input signal and sequentially accessing said programmable memory means at said input signal frequency when said inhibit signal is present and sequentially accessing said programmable memory means at said divided input signal frequency when said inhibit signal is not present.

5. The passive transponder of claim 4, wherein the programmable memory means is a one time programmable memory.

6. The passive transponder of claim 4, wherein the programmable memory means is an EPROM.

7. The passive transponder of claim 1, wherein said transponder has a length no greater than 0.750 inches and a diameter no greater than 0.1 inches.

8. The passive transponder of claim 4, wherein said transponder includes a substrate and a ferrite rod, said receive antenna means comprising a first coil wrapped about said ferrite rod, said transmit antenna means comprising a second coil wrapped about said ferrite rod and said programmable memory means and data sequencing means is a chip mounted on said substrate.

9. The passive transponder of claim 8, wherein said transponder has a length no greater than 0.750 inches and a diameter no greater than 0.1 inches.

10. The passive transponder of claim 1, wherein said transponder is programmed in response to said input signal.

11. The passive transponder of claim 4, wherein said input signal induces a first voltage and a second voltage in said transponder, said second voltage being greater than said first voltage and causing said accessed address of said programmable memory to be programmed when said inhibit signal is not present.

12. The passive transponder of claim 1, wherein said transponder is adapted to be implanted in a host and further comprising monitoring means for monitoring characteristics of the host and outputting characteristic data as an analog signal, said output signal further comprising said characteristic data.

13. The passive transponder of claim 12, wherein said characteristic is the temperature of said host.

14. The passive transponder of claim 13, wherein said monitoring means includes a chip thermistor for detecting the temperature of the host and outputting a resistance in response thereto and temperature to frequency converter means for converting the resistance to a frequency, said output signal including said frequency as said analog signal.

15. The passive transponder of claim 12, further comprising data sequencing means for receiving said input signal and sequentially permitting said characteristic data and said stored data to be output as said output signal in response thereto.

16. The passive transponder of claim 15, wherein said stored data is user selected identification data and said characteristic data is a function of the temperature of said host.

17. The passive transponder of claim 4, wherein said transponder is adapted to be implanted in a host and further comprising monitoring means for monitoring characteristics of the host and outputting characteristic data as an analog signal, said output signal further comprising said characteristic data and wherein said data sequencing means further sequentially permits said characteristic data and said stored data to be output as said output signal in response thereto.

18. The passive transponder of claim 12, wherein said transponder has a length no greater than 0.750 inches and a diameter no greater than 0.1 inches.

19. The passive transponder of claim 17, wherein said transponder includes a substrate and a ferrite rod, said receive antenna means comprising a first coil wrapped about said ferrite rod, said transmit antenna means comprising a second coil wrapped about said ferrite rod and said programmable memory means and data sequencing means is a single chip mounted on said substrate.

20. The passive transponder of claim 1, further comprising frequency generator and modulator means for receiving said input signal and, creating a frequency for said output signal and outputting said output signal in response thereto, said input signal having a first frequency and said output signal having a second frequency.

21. The passive transponder means of claim 19, wherein said monitoring means is a chip thermistor mounted on said substrate.

22. The passive transponder of claim 21, wherein said second frequency is greater than said first frequency.

23. The passive transponder of claim 21, wherein said first frequency is less than 10 KHz.

* * * * *